United States Patent [19]

Hess et al.

[11] 4,135,050

[45] Jan. 16, 1979

[54] PROCESS FOR PREPARING ANTHRANILIC ACID ESTERS

[75] Inventors: Peter Hess, Hofheim am Taunus; Bernhard Mees, Ehlhalten, both of Fed. Rep. of Germany

[73] Assignee: Hoechst Aktiengesellschaft, Frankfurt am Main, Fed. Rep. of Germany

[21] Appl. No.: 823,848

[22] Filed: Aug. 11, 1977

[30] Foreign Application Priority Data

Aug. 13, 1976 [DE] Fed. Rep. of Germany ....... 2636423

[51] Int. Cl.$^2$ ..................... C07C 79/46; C07C 101/54
[52] U.S. Cl. ........................................ 560/19; 560/22; 560/46; 560/47
[58] Field of Search ......................... 560/19, 22, 46, 47

[56] References Cited

U.S. PATENT DOCUMENTS 2,290,128   7/1942   Loder et al. ......................... 560/189

OTHER PUBLICATIONS

Hilgetag et al., Preparative Organic Chem., John Wiley & Sons, p. 375 (1972).
Kirk-Othmer Encyclopedia of Chem. Tech.", 8, John Wiley & Sons, pp. 356-358 (1965).
Groggins, Unit Processes In Organic Synthesis, McGraw-Hill Book Co., Inc. pp. 616-618 (1952).

Primary Examiner—Howard T. Mars
Assistant Examiner—G. T. Breitenstein
Attorney, Agent, or Firm—Curtis, Morris & Safford

[57] ABSTRACT

Anthranilic esters are obtained in good yield and high purity by transesterification when using potassium carbonate as transesterification catalyst.

10 Claims, No Drawings

PROCESS FOR PREPARING ANTHRANILIC ACID ESTERS

The present invention is related to an improved process for preparing anthranilic acid esters of formula I

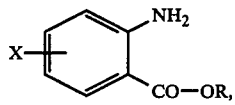

wherein X represents a hydrogen or halogen atom, preferably a chlorine or bromine atom, a hydroxy group, an alkyl radical having from 1 to 4 carbon atoms, an alkoxy radical having from 1 to 4 carbon atoms or a nitro group and R represents a linear or branched alkyl radical having from 2 to 5 carbon atoms, by transesterification of an anthranilic acid alkyl ester in the presence of a basic catalyst.

It is known that anthranilic acid alkyl esters may be obtained by esterification of anthranilic acid with the pertinent alcohols, hydrogen chloride or sulfuric acid being used as catalysts. However, both processes have their disadvantages. For one, at least one mole of the catalyst has to be used in each case, since due to the amine group which is present in the anthranilic acid, the hydrochloride is formed in one case and the alkyl sulfate of the pertinent ester is formed in the other case. The free ester has to be set free from these ammonium salts by adding a base, a requirement which produces large quantities of salts. Another inconvenience of the process is the fact, that hydrogen chloride as a catalyst engages in a side reaction with the present alcohol to form alkyl chloride. The use of sulfuric acid as a catalyst leads to the formation of dialkyl ether. Both by-products represent a source of risk and are, therefore, highly undesirable.

It is also known that anthranilic acid alkyl esters are formed by transesterification of an anthranilic acid ester (as a rule of the methyl ester) with an alcohol, the boiling point of which is higher than that of the alcohol bound in the ester in use. If this transesterification is carried out with an acid catalyst, the same disadvantages occur which have been described for the esterification of anthranilic acid with an acid catalyst.

The reaction of anthranilic acid methyl ester to anthranilic acid menthyl ester under the catalytic action of sodium methylate with a yield of 66% of the theoretical yield is known from U.S. Pat. No. 2,170,185. J. Amer. Chem. Soc. 62, 3136–3139 (1940) describes the transesterification of anthranilic acid methyl ester to yield alkoxy alkyl esters at 62–79% of the theoretical yield, as catalyst being used an alkoxy alcoholate obtained by dissolving sodium in the pertinent alkoxy alcohol. Practice shows, however, that upon transesterification of anthranilic acid methyl esters with higher alcohols ($C_2$ to $C_5$) and sodium methylate as catalyst, dianthranilide (tetrahydrodibenzodiazocindione) and minor portions of higher condensation products are formed due to intermolecular condensation of the anthranilic acid ester. The same by-products are formed, when instead of the methylate the sodium alcoholate of the transesterification alcohol is used. These contaminations are difficult to remove by filtration and their removal is incomplete. Thixotropy of the precipitate brings about long filtration periods, and the filtrates being originally limpid become very turbid again within a short. It is also very difficult to dispose of the considerable residues from the distillation of the products. Anthranilic acid alkyl esters are obtained in a yield of 73 to 82% of the theoretical yield. If one of the starting compounds contains but even a minor quantity of water, these yields are diminishing considerably. In order to keep the formation of undesirable condensation products in somewhat tolerable limits, the alcohol required for the reaction has to be used in a large excess quantity (4 to 7 moles of alcohol per mole of ester). Therefore, the process is unsatifactory on an industrial scale in every respect, such as space-time-yield, purity of the product or profitableness.

It has now been found that the disadvantages which have been described heretofore for transesterification with an alcoholate as catalyst, do not occur, if as the basic catalyst potassium carbonate is used. It has also been found that the use of potassium carbonate as transesterification catalyst reduces considerably the quantities of alcohol required without running the risk of undesirable condensation products being formed. The higher alkyl esters of anthranilic acid are obtained in good yield and are suitable for filtration. The filtrate is not subject to significant tardy turbidity.

The subject of the present invention is thus a process for preparing anthranilic acid esters of formula I by the reaction of an anthranilic acid ester of formula II

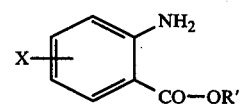

wherein X has the afore given meaning and R' represents an alkyl radical having 1 to 5 carbon atoms, with an alcohol of the formula ROH, wherein R has the afore given meaning, by splitting off the alcohol of the formula R'OH having a lower boiling point, in the presence of a basic transesterification catalyst, which comprises the transesterification catalyst being potassium carbonate.

Some preferred embodiments of the present invention are described as follows:

The anthranilic acid ester (II) to be transesterified is reacted with the alcohol ROH in a molar ratio of 1:1.5 to 1:5, preferably 1:2, and with 1 to 10, preferably 2 to 5 mole-% of potassium carbonate, referred to anthranilic acid ester (II), in such a way that the reaction mixture is heated just below the boiling point of the alcohol ROH and that the alcohol R'OH set free from the ester is distilled off, possibly over a column. In some cases preference may be given to reflux the transesterification mixture for a while prior to distilling off the liberated alcohol. Subsequently the excess quantity of alcohol ROH used for the transesterification is distilled off, which distillation may be carried out also under reduced pressure. The ester (I) is then separated from the catalyst residue by filtration, the filtration periods being regularly very short. This method yields an ester (I) that may be used for many purposes without any additional purification.

Preferably are used as the ester of formula (II), the methyl ester and as the alcohol ROH n-butanol.

By distillation in vacuo of the non-filtered crude ester (I), very good yields of pure alkyl ester (88–97% of the theoretical yield) are obtained, while the minor distillation residue is easily removed from the distillation vessel with a little water.

The excellent catalytic action of potassium carbonate is all the more surprising, since neither sodium carbonate nor lithium carbonate are sufficiently active.

The process according to the invention provides a simple and profitable possibility for preparing higher alkyl esters of anthranilic acid which represent valuable intermediates for pharmaceutical purposes, perfumery and dyestuffs.

In the following Examples all parts and percentages are by weight unless otherwise stated.

EXAMPLE 1

453 parts of anthranilic acid methyl ester are refluxed with 900 parts of ethanol and 30 parts of potassium carbonate for half an hour. Methanol which is set free during the reaction is then distilled off over a column. The complete transesterification requires about 20 hours. After an intermediate fraction containing methanol and ethanol as well, the excess of ethanol is distilled off. By distillation of the residue under reduced pressure there are obtained 441 parts of anthranilic acid ethyl ester (boiling point 113°–122° C. under 3–5 mm Hg, $n_D^{25}$ 1,564; anthranilic acid methyl ester cannot be traced by gas chromatography). The yield is 89% of the theory.

EXAMPLE 2

453 parts of anthranilic acid methyl ester are reacted with 900 parts of n-propanol and 15 parts of potassium carbonate according to Example 1. The reaction lasts for about ten hours. There are obtained 495 parts of anthranilic acid-n-propyl ester (boiling point 128°–131° C. at 3–5 mm Hg; $n_D^{25}$ 1,551; containing according to gas chromatography less than 0.2% of anthranilic acid methyl ester). The yield is 92% of the theory.

EXAMPLE 3

467 parts of anthranilic acid ethyl ester are heated with 1000 parts of isobutanol and 10 parts of potassium carbonate. The separated ethanol is distilled off over a column, this operation requiring about eight hours. After collecting an intermediate fraction being the mixture of both alcohols, the excess quantity of isobutanol is distilled off, the remaining residual quantity being removed in vacuo. The catalyst is filtered off. There are obtained 556 parts of anthranilic acid isobutyl ester ($n_D^{25}$ 1.540; anthranilic acid ethyl ester content according to gas chromatography below 2%). The filtrate maintains its limpid character even at prolonged storage. The yield is 96% of the theory.

EXAMPLE 4

453 parts of anthranilic acid methyl ester, 444 parts of n-butanol and 11 parts of potassium carbonate are heated together and the methanol thus formed is distilled off over a column. A subsequent intermediate fraction contains both methanol and n-butanol. Finally, the excess quantity of n-butanol is distilled off, preferably in vacuo towards the end of this operational step. The reaction time lasts for about 8 hours. After filtration of the catalyst there are obtained 562 parts of anthranilic acid n-butyl ester ($n_D^{25}$ 1.545; accoding to gas chromatography of 99–100% purity). Yield: 97% of the theory.

EXAMPLE 5

453 parts of anthranilic acid methyl ester, 444 parts of n-butanol and 11 parts of potassium carbonate are heated together, the methanol thus formed is distilled off over a column. After an intermediate fraction containing methanol and n-butanol, the excess quantity of n-butanol is distilled off, towards the end this latter operational step is carried out in vacuo. The reaction lasts for about nine hours. The residue is distilled in vacuo, there are obtained 556 parts of pure anthranilic acid n-butyl ester (boiling point 130°–140° C. under 7 mm Hg, $n_D^{25}$ 1.544, purity according to gas chromatography 99–100%). Yield: 96% of the theory.

EXAMPLE 6

450 parts of anthranilic acid methyl ester, 500 parts of n-pentanol and 10 parts of potassium carbonate are reacted as described in Example 1. The reaction lasts for about 8 hours. There are obtained 588 parts of anthranilic acid n-pentyl ester (boiling point 132°–135° C. under 0.3–0.4 mm Hg; $n_D^{25}$ 1.538; purity according to gas chromatography 99%, below 0.2% of anthranilic acid methyl ester). Yield: 95% of the theory.

EXAMPLE 7

186 parts of 5-chloroanthranilic acid methyl ester, 150 parts of n-butanol and 10 parts of potassium carbonate are refluxed for half an hour. The separated methanol is then distilled off over a column. Distillation is continued until the boiling point of n-butanol is reached, then after addition of 4 parts each of bleaching earth and of active charcoal the hot mixture is filtered and agitated with 100 parts of acetone and 200 parts of ice. The reaction lasts for about 6 hours. The precipitate is filtered off, washed with ice-cold water and dried in vacuo at room temperature. There are obtained 211 parts of 5-chloroanthranilic acid-n-butyl ester, melting point 37°–39° C. The yield is 93% of the theory.

EXAMPLE 8

210 parts of 5-nitroanthranilic acid ethyl ester, 210 parts of n-butanol and 10 parts of potassium carbonate are refluxed for half an hour. The thus formed ethanol is then distilled off over a column. Distillation is continued until the boiling point of n-butanol is reached. 450 parts of cyclohexane are then added, and after addition of 4 parts each of bleaching earth and active charcoal the hot mixture is filtered, followed by cooling to 0° C. The reaction lasts for about 4 hours. The precipitate is filtered off, washed with about 100 parts of cyclohexane and dried in vacuo at 60° C. There are obtained 222 parts of 5-nitroanthranilic acid-n-butyl ester, melting point 91°–93° C. The yield is approximately 93% of the theory.

We claim:

1. In a process for the preparation of an anthranilic ester of the formula I

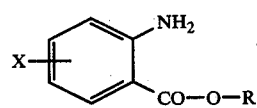

in which R is alkyl of 2 to 5 carbon atoms and X is hydrogen, chlorine, bromine, alkyl of 1 to 4 carbon atoms, alkoxy of 1 to 4 carbon atoms or nitro, by transesterifying an ester of the formula II

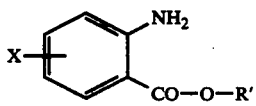

in which X is defined as above and R' is alkyl of 1 to 5 carbon atoms, with an alcohol of the formula III

in which R is defined as above, by splitting off an alcohol of the formula IV

in which R' is as defined above, the alcohol of the formula IV being split off having a lower boiling point than the alcohol of the formula III, with the aid of an alkaline transesterification catalyst, the improvement comprising catalyzing said transesterification with potassium carbonate.

2. A process as claimed in claim 1, wherein 1 to 10 mol-% of potassium carbonate, based on anthranilic ester of formula II, is added to the reaction mixture.

3. A process as claimed in claim 2, wherein 2 to 5 mol-% of potassium carbonate is added.

4. A process as claimed in claim 1, wherein R' is methyl.

5. A process as claimed in claim 1, wherein per each mol of anthranilic ester of formula II 1.5 to 5 mols of alcohol of formula III are present in the initial reaction mixture.

6. A process as claimed in claim 5, wherein 2 mols of alcohol of formula III are present.

7. A process as claimed in claim 1, wherein R is n-butyl.

8. A process as claimed in claim 1, wherein R is n-propyl.

9. A process as claimed in claim 1, wherein R is n-pentyl.

10. A process as claimed in claim 1, wherein R is isobutyl.

* * * * *